United States Patent [19]

Au et al.

[11] Patent Number: 5,336,765

[45] Date of Patent: * Aug. 9, 1994

[54] PROCESS OF PREPARING N-SUBSTITUTED ALDOBIONAMIDES

[75] Inventors: Van Au, Peekskill, N.Y.; Bijan Harirchian, South Orange, N.J.

[73] Assignee: Lever Brothers Company, Division of Conopco, Inc., New York, N.Y.

[ * ] Notice: The portion of the term of this patent subsequent to Mar. 22, 2011 has been disclaimed.

[21] Appl. No.: 23,529

[22] Filed: Feb. 26, 1993

Related U.S. Application Data

[63] Continuation-in-part of Ser. No. 816,422, Dec. 13, 1991, abandoned.

[51] Int. Cl.$^5$ .............................................. C07H 15/00
[52] U.S. Cl. .................................... 536/18.5; 536/172
[58] Field of Search ............................. 536/18.5, 17.2

[56] References Cited

U.S. PATENT DOCUMENTS

| | | |
|---|---|---|
| 2,662,073 | 12/1953 | Mehltretter et al. |
| 2,746,916 | 5/1956 | Magariello |
| 2,752,334 | 6/1956 | Walton |
| 4,774,231 | 9/1988 | Petitou et al. |

FOREIGN PATENT DOCUMENTS 2227008  11/1974  France.

OTHER PUBLICATIONS

European Search Report in European Patent Application 92204033.2.
Dewent Abstract of FR 2.227.008.
Taravel, Francois R., "Amphiphilic Properties of Synthetic Glycolipids Based on Amide linkages, 4", Makromol. Chem., vol. 191, (1990), pp. 3097–3106.
Patent Abstracts of Japan, vol. 015163, JP 3034946.
Ullmann's Encyclopedia of Industrial Chemistry, vol. A14: Immobilized Biocatalysts to Isoprene, (1989), pp. 448–449.
Kobayashi, Kazukiyo, et al., "Synthesis and Functions of Polystyrene Derivatives Having Pendant Oligosaccharides", Polymer Journal, vol. 17, No. 4, (1985), pp. 567–575.
Williams, Taffy J., et al., "A New Class of Model Glycolipids: Synthesis, Characterization, and Interaction with Lectins", Archives of Biochemistry and Biophysics, vol. 195, No. 1, (Jun. 1979), pp. 145–151.
Ziegast, Gerd et al., "Coupling of Mono– and Oligosaccharides to $\delta,\omega$–Diamino Substituted Poly(oxyethylene) and Multifunctional Amines by Amide Linkage", Makromol. Chem., Rapid Commun., vol. 5, (1984), pp. 373–379.

*Primary Examiner*—Herbert J. Lilling
*Attorney, Agent, or Firm*—Rimma Mitelman

[57] ABSTRACT

A process of preparing aldobionamides and N-substituted aldobionamides which includes the steps of recovering a by-product of the process (an ammonium salt of an aldobionic acid) and converting it into at least one starting material. Aldobiono-1,5-lactone is reacted with a primary or secondary amine and the resulting solution containing the by-product of the reaction is passed through an anionic exchange column to obtain the eluate containing the starting amine and some aldobionamide. The eluate may be recycled as part of the starting material mixture. Alternatively, the amine and the aldobionamide may be recovered from the eluate, and the amine alone may be recycled. Aldobionate anion is retained on the column and may be converted into the salt of an aldobionic acid and then into the aldobionic acid.

20 Claims, No Drawings

PROCESS OF PREPARING N-SUBSTITUTED ALDOBIONAMIDES

This application is a continuation in part of application Ser. No. 07/816,422 filed Dec. 31, 1991, now abandoned.

FIELD OF THE INVENTION

The invention relates to an improved process of preparing N-substituted aldobionamides.

RELATED ART

Aldobionamides are defined as the amide of an aldobionic acid. An aldobionic acid is a sugar substance (e.g., any cyclic sugar) wherein the aldehyde group (generally found at the $C_1$ position of the sugar) has been replaced by a carboxylic acid. Aldobionamides are based on compounds comprising more than one saccharide unit; they may be based on compounds comprising two saccharide units (e.g., lactobionamide or maltobionamide) or they may be based on compounds comprising more than two saccharide units as long as the polysaccharide has a terminal sugar unit with an aldehyde group available for oxidation.

Walton et al. (U.S. Pat. No. 2,752,334) discloses a process for the preparation of the N-substituted lactobionamides by reacting the corresponding organic primary or secondary amine with lactobiono-1,5-lactone. The reaction is effected by heating the reactants with a solvent in the case of the amines having a higher boiling point. However, the use of a solvent and lower temperature is said to give better yields with less chance of decomposition in the course of the reaction and therefore a purer product. Reaction temperatures within the range from 65° to 140° C. are said to be preferred. Yields of from 70 to 75% were reported.

Kobayashi et al., "Synthesis and Functions of Polystyrene Derivatives Having Pendant Oligosaccharides," Polymer Journal, Vol. 17, No. 4, 567–575 (1985), describe a process wherein a lactone is dissolved in refluxing methanol and a solution of amine in ethanol is added. The mixed solution is refluxed for two hours. 82% yield was reported.

Williams et al., "A new Class of Glycolipids: Synthesis, Characterization, and Interaction with Lectins," Archives of Biochemistry and Biophysics, Vol. 195, No. 1, June, 145–151, 1979, describe a process wherein a lactone was dissolved in methanol by gentle heating, an amine was added, and the reaction mixture was stirred overnight at room temperature. 70% yield was reported.

Ziegast et al., "Coupling of Mono- and Oligosaccharides to δ-w-diamino substituted Poly(oxyethylene) and Multifunctional Amines by Amide Linkage", Makromol Chem., Rapid Commun. 5, 313–379 (1984) disclose the procedure for coupling of carbohydrates to various compounds: saccharide is converted into the aldonic acid lactone via electrolytic oxidation and subsequent binding to an amino group containing carrier by amide linkage. The reaction according to Ziegast et al. requires an excess of lactone, which is subsequently separated by using relatively strong basic ion exchange column. Ziegast et al. employ an excess of lactone and conduct the reaction at 70° C. or above.

Aldobionamides are carbohydrate-based molecules and, as such, represent a source of renewable raw materials that are synthetically versatile and environmentally friendly. Aldobionamides have useful physical properties (e.g., surfactancy) which makes them suitable for many applications in personal care, dental, detergent and cosmetic areas. Surfactant compositions incorporating aldobionamides have been described in a commonly assigned application, Ser. No. 07/981,737, incorporated by reference herein. In light of a potentially large demand for aldobionamides, it is desirable to improve the efficacy of processes of their production. Prior art processes discussed above result in formation of 20–30% of by-products, which were not utilized and not even identified.

Accordingly, it is an object of the invention to provide an improved process of manufacturing aldobionamides.

It is another object of the invention to provide a process of preparing aldobionamides wherein a by-product of the process is converted to at least one starting materials required in the process.

It is yet another object of the invention to provide a continuous process of preparing aldobionamides.

These and other objects of the invention will become more apparent from the detailed description and examples that follow.

SUMMARY OF THE INVENTION

The above objects are accomplished by the present invention which includes a process of preparing an N-substituted aldobionamide, the process including steps of:

i) preparing a homogeneous mixture containing an aldobionolactone, an organic polar solvent, and an amine $HNR^1R^2$, wherein $R^1$ and $R^2$ are the same or different and are selected from the group consisting of hydrogen, an aliphatic hydrocarbon radical, an aromatic radical, a cycloaliphatic radical, and mixtures thereof, except that $R^1$ and $R^2$ are not both hydrogen at the same time, wherein the molar ratio of the aldobionolactone to the amine is in the range of from 1:1.5 to 1:1;

ii) reacting the homogeneous mixture at a temperature not greater than 65° C. to obtain a reaction product including a solution comprising the aldobionamide and a corresponding ammonium salt of an aldobionic acid; and iii) passing the solution through an anionic exchange column and eluting the column with an organic polar solvent to obtain an eluate containing the starting amine and the aldobionamide.

The eluate may be recycled as part of the starting material mixture, although the eluate contains aldobionamide which is not a required starting ingredient. Alternatively, the amine and the aldobionamide may be recovered from the eluate, and the amine alone may be recycled.

Preferably, the process according to the present invention is continued to recover an aldobionic acid: the column is washed with base and eluted with water to obtain an aldobionic acid salt, which in turn may be converted to the aldobionic acid. Aldobionic acid may in turn be converted to the aldobionolactone utilized as a starting ingredient in the inventive process.

Any N-substituted aldobionamide may be synthesized according to the present process, as long as a particular primary or secondary amine $HNR^1R^2$ required to produce that aldobionamide is available commercially or can be synthesized.

The inventive process is improved compared to the prior art processes because it converts a previously unidentified and unutilized by-product, the ammonium salt of the aldobionic acid, into one or more compounds which may be employed in a variety of reactions. Preferably, the resulting compounds are employed as starting materials (i.e., recycled) in the inventive process, in which case the aldobionamides may be synthesized via a continuous process.

DETAILED DESCRIPTION OF THE INVENTION

The inventive process is suitable for synthesis of any N-substituted aldobionamide. Examples of aldobionamides include but are not limited to lactobionamides, maltobionamides, cellobionamides, melibionamides, gentiobionamides and the like.

Starting materials employed in the inventive process include an aldobionolactone, a primary or secondary amine carrying the desired $R^1$ and $R^2$ groups, and an organic polar solvent. Any organic polar solvent is suitable, for example aliphatic alcohols, glycols and glycol monoethers, such as methanol, ethanol, isopropanol, ethylene glycol, polyethylene glycol, triethylene glycol, diethylene glycol, diethylene glycol monoethyl ether, ethylene glycol monobutyl ether, ethylene glycol monoethyl ether, ethylene glycol monomethyl ether, diethylene glycol monobutyl ether, and triethyene glycol monomethyl ether. Of course, other polar solvents not listed above may be employed.

Aldobionolactones may be obtained commercially, (e.g., from Aldrich Chemicals) or they may be prepared by dissolving an aldobionic acid in an organic solvent such as dioxane or methanol. Preparation of aldobionolactones is described in a greater detail by Williams et al., "A new Class of Glycolipids: Synthesis, Characterization, and Interaction with Lectins," Archives of Biochemistry and Biophysics, Vol. 195, No. 1, June, 145–151, 1979 and by H. S. Isbell, Bureau of Standards, Journal of Research, Vol. 11, 1933 which disclosures are incorporated by reference herein. Alternatively, aldobionolactones may be obtained by spray drying an aqueous solution as described in U.S. Pat. No. 2,746,916, incorporated by reference herein. An aldobionolactone preferably employed in the present invention is an aldobiono-1,5-lactone.

The amine, $HNR^1R^2$, may be obtained commercially (Aldrich Chemicals) as in the case of aliphatic amine, or it may be synthesized. When aliphatic amines are employed $R^1$ and/or $R^2$ contain at least 3 carbon atoms to ease synthesis (amines wherein $R^1$ and/or $R^2$ contain fewer than 3 carbon atoms have to be bubbled in due to their high volatility).

An example of the reaction employed in the inventive synthesis is as follows:

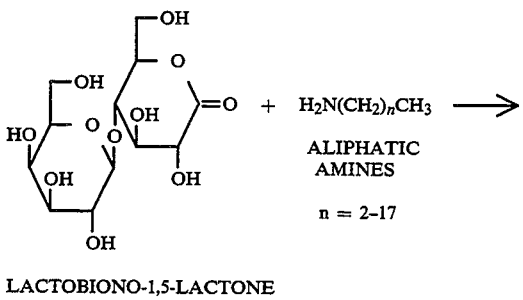

LACTOBIONO-1,5-LACTONE

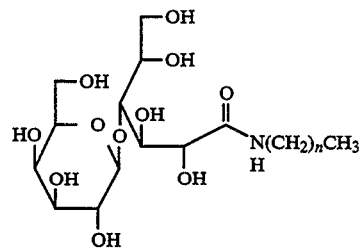

N-ALKYL LACTOBIONAMIDES

The aldobionolactone and the amine constitute 10–40% by weight of the starting reaction mixture, and the solvent constitutes 60–90% by weight. Preferably, the aldobionolactone and the amine constitute from about 20% to about 30% of the starting reaction mixture. The molar ratio of the aldobionolactone to the amine is in the range of from 1:1.5 to 1:1, preferably in the range of from 1:1.3 to 1:1. Most preferably, the molar ratio of the aldobionolactone to the amine in the starting reaction mixture is 1:1.

In the first step of the inventive process a homogeneous mixture of starting materials is prepared. Preferably, in order to facilitate the formation of the homogeneous mixture the solvent is slightly heated, typically to a temperature in the range of from 25° to 65° C., preferably in the range of from about 25° C. to 50° C.

It is preferred, in order to optimize purity, that a mixture of the aldobionolactone in the solvent is prepared first, with stirring, preferably in a warm solvent. The aldobionolactone may be completely dissolved in the solvent, although more frequently only a partial dissolution occurs. The amine, $HNR^1R^2$, is subsequently added, with stirring, preferably gradually or in several portions, in order to attain the homogeneity of the mixture and to optimize the purity of the product. The stirring is conducted with a magnetic stirrer or with an overhead stirrer at moderate rpm. The amine may be added neat (i.e., liquid or melted) or it may be added as a solution in the same solvent that was combined with the aldobionolactone.

The resulting homogeneous mixture is reacted to obtain a reaction product including a solution containing at least some of the product, N-substituted aldobionamide and a by-product, a corresponding ammonium salt of an aldobionic acid. The stirring is typically continued at the same rate as that employed during the mixing step. The reaction may be conducted at room temperature or at an increased temperature. Typically, the reaction temperature is in the range of from about 25° C. to about 65° C., preferably in the range of from about 25° C. to about 50° C., most preferably in the range of from about 25° C. to about 40° C. It is essential to carry out the reaction at a temperature not greater than 65° C. in order to minimize heat decomposition as well as base induced β-elimination. For the same reason, it is important that in the first (mixing) step the temperature does not exceed 65° C. either.

The product, N-substituted aldobionamide, may or may not precipitate out of solution. Typically, at least pad of N-substituted aldobionamide is present in the solution. When the precipitate is formed, it is separated from the solution. The separation may be conveniently carried out by filtering the precipitate out (by gravity or vacuum filtration), although other separation techniques, e.g. centrifugation, may be employed. The product, N-substituted aldobionamide, is washed with a suitable solvent and dried. The inventive process typically results in yields of N-substituted lactobionamides in the range of from about 80% to about 95%. Further steps of the inventive process are carried out on the obtained solution.

The present invention is based, in part, on the discovery that a by-product contained in the solution consists predominantly of an ammonium salt of aldobionic acid: the ammonium salt typically constitutes from about 5% to about 20% by weight of the solid contained in the solution). The inventive process aims to convert the by-product into compounds which may be used as starting materials in a variety of reactions. The by-product is preferably converted into the starting materials for the inventive process, i.e., the aldobionolactone and the amine.

According to the inventive process, the solution is passed through an anionic exchange column. Suitable anionic exchange resin columns are as follows: Dowex®, Amberlite®, such as Dowex 1×2® and Dowex 1-8® and Amberlite IRA-400® and Amberlite 401® and other strongly basic resins. The amount of resin to be used is generally calculated according to the capacity of the resin (usually expressed in milliequivalents per gram of resin). Typically, a slight excess (up to about 20% excess) over the calculated amount is employed.

The column is then eluted with an organic polar solvent in order to recover the amine $HNR^1R^2$ and any N-substituted aldobionamide that may be contained in the solution. Requirements for the solvent in this step are similar to the requirements for the solvent in preparing the initial reaction mixture, i.e., an organic polar solvent is employed. The volume of the solvent to be used for elution is determined by monitoring the content of the ammonium salt in the eluate. The monitoring can be accomplished by a number of analytical methods, e.g. pH measurement or spectroscopy). Preferably, the same solvent is employed in the eluting step as in the reaction. Preferably, methanol is employed as eluting solvent because of its availability at low cost and its low boiling point (easier to remove). The N-substituted aldobionamide and the amine may be recovered by evaporating the solvent.

The combined recovered amine and aldobionamide may be recycled (with or without the solvent) as the starting ingredients of the inventive process. The amine may be separated from the aldobionamide by evaporating the solvent and washing the residue with a nonpolar solvent, e.g. acetone or isopropanol. The aldobionamide is left as the residue.

An aldobionate anion is retained on the column. The column may and preferably is then washed with a base and eluted with water in order to recover the salt of aldobionic acid. Suitable base is any alkaline metal hydroxide, i.e., KOH, NaOH, $Ca(OH)_2$, $Mg(OH)_2$. Typically, 1N base is used, but the range of about 0.05N to 2N is suitable. Distilled deionized water is typically employed in this step.

The recovered salt of aldobionic acid is preferably then converted into aldobionic acid by a variety of methods, for instance acidification with acids such as HCl, $H_2SO_4$ and the like. The preferred method of converting the salt into aldobioninc acid is by passing the salt through a cationic exchange column; this method is preferred because it avoids formation of NaCl and converts any NaOH present in the eluate to water. Suitable cationic exchange resin columns are as follows:

Dowex® and Amberlite®, such as Dowex 50X® and Amberlite IRP.69® and other strongly acidic resins.

In the inventive process, $R^1$ and $R^2$ groups on the starting amine, $HNR^1R^2$, are attached to the nitrogen of an aldobionamide. Thus, depending on the particular amine employed, a variety of N-substituted aldobionamides may be synthesized according to the inventive process. Preferably, in order to simplify synthesis and reduce cost, $R^1$ is hydrogen, thus a primary amine is employed. For the sake of clarity, examples of various substituted aldobionamides will be given below using lactobionamide of Formula A and maltobionamide of Formula B as an illustration. The corresponding ammonium salts of lactobionamide and maltobionamide are illustrated by Formula C and Formula D, respectively.

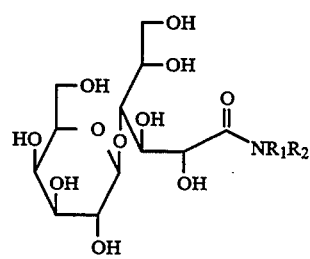

FORMULA A

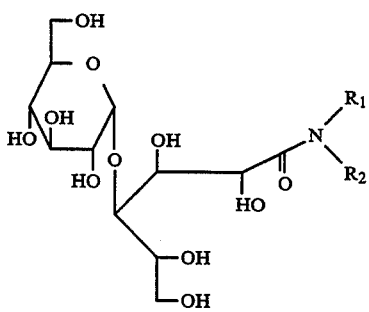

FORMULA B

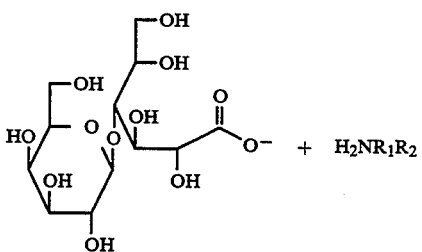

FORMULA C

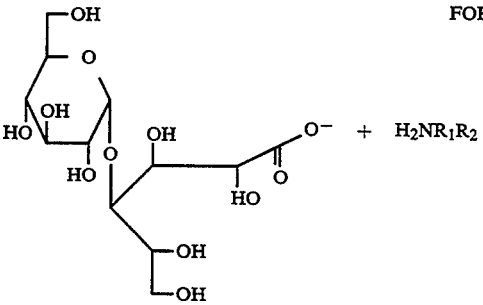

FORMULA D

N-alkyl lactobionamides are compounds of Formula A wherein $R^1$ and/or $R^2$ is an aliphatic hydrocarbon radical. Suitable aliphatic hydrocarbon radicals include saturated and unsaturated radicals including but not limited to methyl, ethyl, amyl, hexyl, heptyl, nonyl, decyl, undecyl, dodecyl, tridecyl, tetradecyl, pentadecyl, hexadecyl, heptadecyl, octadecyl, coco, tallow, soya, allyl, undecenyl, oleyl, linoleyl, linolenyl, propenyl, and heptenyl. The active compounds of the inventive compositions may contain straight or branched aliphatic groups. Aromatic radicals are exemplified by benzyl, aniline, or substituted benzyl or aniline groups. Suitable mixed aliphatic aromatic radicals are exemplified by benzyl, phenyl ethyl, phenoxy ethyl, and vinyl benzyl. Cycloaliphatic radicals are exemplified by but not limited to cyclopentyl and cyclohexyl.

N-alkyl lactobionamides, typically contain up to 36 carbon atoms in $R^1$ and $R^2$ groups, preferably up to 24 carbon atoms, most preferably from 8 to 18 carbon atoms, and optimally from 10 to 16 carbon atoms in order to attain optimum surface activity.

Of course, other $R^1$ and $R^2$ radicals not listed above but within the scope of the claims may be employed.

N-substituted maltobionamides, cellobionamides, melibionamides, gentibionamides and other aldobionamides analogous to N-substituted lactobionamides discussed in detail above may be produced according to the present invention, as long as a particular primary or secondary amine, which is necessary to deliver the desired $R^1$ and/or $R^2$ group to the nitrogen atom of the aldobionamide is commercially available or can be synthesized.

The following specific examples further illustrate the present invention, but the invention is not limited thereto.

Dodecyl and tetradecylamines (99–96%) were obtained from Aldrich Chemicals and A.C.S. certified grade methanol which contained 0.02–0.1% of water was used. Dowex ® styrene benzene quaternary ammonium functional group and styrene divinyl benzene sulfonic functional group were used as ionic exchange resins.

EXAMPLE 1

Tetradecylammonium lactobionate

Lactobiono-1,5-lactone (20 g, 1 eq) was dissolved in water (150 ml) at 70° C. Tetradecylamine (12.5 g, 1 eq)in 50 ml of methanol was added dropwise. The resulting solution was evaporated on a rotary evaporator to remove methanol. The resulting mixture was freeze-dried to give 30 grams of tetradecylammonium lactobionate. Tetradecylammonium lactobionate was characterized by NMR and mass spectroscopy.

N-tetnadecyl Lactobionamide

In a 5 L three necked round bottom flask equipped with a condenser and mechanical stirrer, lactobiono-1,5-lactone (400 g) was dissolved in warm methanol (3.5 L, 50°–55° C.). Melted tetradecylamine (1.0 eq, 272 g) was then added gradually in 3 portions. The reaction was cooled to room temperature followed by stirring overnight to allow complete crystallization. The desired white product was filtered and recrystallized from methanol in 91% (550 g) isolated yield. The methanol filtrate contained a mixture of N-tetradecyl lactobionamide and tetradecylammonium lactobionate (identified by NMR and mass spectroscopy and by comparison with synthesised tetradecyl ammonium lactobionate).

EXAMPLE 2

Dodecylammonium lactobionate

Lactobiono-1,5-lactone (13.2 g, 1 eq) was dissolved in water (150 ml) at 70° C.; dodecylamine (7.2 g, 1 eq) in 50 ml MeOH was added slowly. The resulting solution was rotary evaporated to remove MeOH, followed by freeze-drying to give 20 g of dodecylammonium lactobionate. Dodecylammonium lactobionate was characterized by NMR and mass spectroscopy.

N-dodecyl lactobionamide

N-dodecyl lactobionamide was prepared according to the procedure described in Example 1 for N-tetradecyl lactobionamide. The isolated yield after recrystallization was 84%. The methanol filtrate contained a mixture of N-dodecyl lactobionamide and dodecylammonium lactobionate (identified by NMR and mass spectroscopy and by comparison with synthesised dodecyl ammonium lactobionate).

EXAMPLE 3

Comparative Example

In a three necked (5.0 L) round bottom flask equipped with a condenser and a mechanical stirrer, tetradecylamine (204 g, 1.0 eq) was dissolved in warm methanol (50° C., 1000 g). Lactobiono-1,5-lactone (300 g, 1.0 eq) was added and the reaction was heated at 70°–75° C. for one hour. Activated charcoal was added (40 g) and the solution was filtered hot. The solution was cooled overnight and the resulting product of yellow color was filtered and washed with methanol (750 ml), diethyl ether, (750 ml) and dried in vacuum at 40° C. The yield was about 51% after recrystallization.

Examples 1 and 2 demonstrate that a by-product obtained during the formation of N-substituted aldobionamide is an ammonium salt of the aldobionic acid. Examples 1 and 2 demonstrate that improved yields are obtained when aldobiono-1,5-lactone is first mixed with the solvent, and the amine is added subsequently and gradually, as compared to the procedure of Example 3 wherein tetradecylamine was dissolved first. Further, it can be seen from Examples 1 and 2 which are within the scope of the invention and from Example 3 which is not within the scope of the invention that the use of reaction temperature above 65° C. resulted in low yield and colored precipitate, while the use of reaction temperatures below 65° C. results in high yield of purer products.

EXAMPLE 4

In a 12 L three necked round bottom flask equipped with a condenser and a mechanical stirrer, lactobiono-1,5-lactone (919 g, 1.0 eq) was partially dissolved in warm methanol (50°–55° C., 8.2 L). Melted dodecylamine (500 g, 1 eq) was added in three equal portions. Stirring was continued until a homogeneous solution was obtained. The mixture was cooled to room temperature with slow stirring until sufficient amount of precipitate occurred. The reaction was left standing at room temperature overnight. The granule shaped N-dodecyl lactobionamide was filtered and washed with methanol and acetone. The white product was isolated in 84% yield (1066 g) after drying.

The methanol filtrate which contained dodecyl ammonium lactobionate and dodecyl lactobionamide was passed through an anionic exchange column. The column was eluted with methanol. The solvent was evaporated from the resulting eluate. Dodecylamine was separated by washing the residue with acetone. The column was then washed with 1N NaOH and eluted with distilled deionized water to collect the sodium salt of lactobionic acid. The salt was converted to lactobionic acid by a cationic exchange column. All the materials which were separated by the ionic exchange columns are the actual starting materials used for the preparation of dodecyl lactobionamide and can be recycled.

EXAMPLE 5

N-dodecyl maltobionamide

Maltobiono-1,5-lactone (100 g, 1 eq) is dissolved in warm methanol (590 ml, 50°–55° C.) until approximately ⅔ of the lactone is in solution. Melted dodecylamine (55 g, 1 eq) is added in 3 equal portions, with stirring. The resulting solution is cooled to room temperature with slow stirring until sufficient amount of precipitate forms. The reaction mixture is left standing at room temperature overnight. The N-dodecyl maltobionamide is filtered, washed with methanol and acetone.

The methanol filtrate which contains dodecyl ammonium maltobionate and some N-dodecyl maltobionamide is eluted through an anionic resin column, the ammonium salt of maltobionic acid is converted to free amine by this process. The resin is washed with 1N NaOH and eluted with distilled deionized water to collect the sodium salt of maltobionic acid. The salt is converted to maltobionic acid by a cationic exchange resin column.

It should be understood that the specific forms of the invention herein illustrated and described are intended to be representative only. Changes, including but not limited to those suggested in this specification, may be made in the illustrated embodiments without departing from the clear teachings of the disclosure. Accordingly, reference should be made to the following appended claims in determining the full scope of the invention.

What is claimed is:

1. A process of preparing an N-substituted aldobionamide, the process comprising the steps of:
    i) preparing a homogeneous mixture comprising an aldobionolactone, an organic polar solvent, and an amine $HNR^1R^2$, wherein $R^1$ and $R^2$ are the same or different and are selected from the group consisting of hydrogen, an aliphatic hydrocarbon radical, an aromatic radical, a cycloaliphatic radical, and mixtures thereof, except that $R^1$ and $R^2$ are not both hydrogen at the same time, wherein the molar ratio of the aldobionolactone to the amine is in the range of from about 1:1.5 to about 1:1;
    ii) reacting the homogeneous mixture at a temperature not greater than 65° C. to obtain a reaction product including a solution comprising the aldobionamide and a corresponding ammonium salt of an aldobionic acid; and
    iii) passing the solution through an anionic exchange column and eluting the column with an organic polar solvent to obtain an eluate comprising the starting amine and the aldobionamide.

2. The process of claim 1 further comprising washing the anionic exchange column with base and eluting the column with water to obtain the aldobionic acid salt and converting the salt to an aldobionic acid.

3. The process of claim 2 wherein the aldobionic acid salt is converted to the aldobionic acid by passing the salt through a cationic exchange column.

4. The process of claim 3 further comprising preparing the aldobionolactone from the aldobionic acid.

5. The process of claim 1 further comprising the steps of removing the polar organic solvent from the eluate to obtain the residue and washing the residue with a nonpolar solvent to obtain the starting amine.

6. The process of claim 1 wherein the reaction product in step (ii) further comprises a precipitate of the aldobionamide.

7. The process of claim 6 further comprising separating the precipitate from the solution.

8. The process of claim 1 wherein the mixing is conducted at a temperature in the range of from 25° C. to 65° C.

9. The process of claim 1 wherein the aldobionolactone is an aldobiono-1,5-lactone.

10. The process of claim 1 wherein the reaction in step (ii) is conducted at a temperature in the range of 25° to 65° C.

11. The process of claim 1 wherein the reaction in step (ii) is conducted at a temperature not greater than 50° C.

12. The process of claim 1 wherein the solvent is selected from the group comprising methanol, ethanol, isopropanol, ethylene glycol, polyethylene glycol, triethylene glycol, diethylene glycol, diethylene glycol monethyl ether, ethylene glycol monobutyl ether, ethylene glycol monoethyl ether, ethylene glycol monomethyl ether, diethylene glycol monobutyl ether, and triethyene glycol monomethyl ether.

13. The process of claim 1 further comprising recycling the eluate as part of the starting material mixture.

14. The process of claim 1 wherein $R^1$ is hydrogen.

15. The process of claim 1 wherein the aldobionamide is selected from the group consisting of lactobionamides, maltobionamides, cellobionamides, melibionamides, and gentiobionamides.

16. The process of claim 1 wherein $R^2$ is an aliphatic hydrocarbon radical selected from the group consisting of a saturated and an unsaturated radicals, branched and straight radicals.

17. The process of claim 1 wherein $R^1$ and $R^2$ are the same or different and both together include from 1 to 36 carbon atoms.

18. The process of claim 1 wherein $R^1$ is hydrogen and $R^2$ is an aliphatic hydrocarbon radical containing from 1 to 36 carbon atoms.

19. The process of claim 1 wherein the aldobionamide is N-alkyl lactobionamide.

20. The process of claim 19 wherein N-alkyl lactobionamide has an alkyl chain having from 1 to 20 carbon atoms.

* * * * *